US00PP26728P3

(12) United States Plant Patent
Braunig

(10) Patent No.: US PP26,728 P3
(45) Date of Patent: May 10, 2016

(54) ***SALVIA* PLANT NAMED 'FLORSALBRO'**

(50) Latin Name: *Salvia nemerosa*
Varietal Denomination: Florsalbro

(71) Applicant: Tobias Braunig, Quedlinburg (DE)

(72) Inventor: Tobias Braunig, Quedlinburg (DE)

(73) Assignee: Florensis B.V. (NL)

( * ) Notice: Subject to any disclaimer, the term of this patent is extended or adjusted under 35 U.S.C. 154(b) by 120 days.

(21) Appl. No.: 14/120,816

(22) Filed: Jun. 30, 2014

(65) Prior Publication Data

US 2015/0382530 P1 Dec. 31, 2015

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Cassandra Bright

(57) ABSTRACT

A new and distinct *Salvia* cultivar named 'Florsalbro' is disclosed, characterized by a compact form, early flowering and abundant dark rose colored flowers. The new variety is a *Salvia*, normally produced as an outdoor garden or container plant.

2 Drawing Sheets

Latin name of the genus and species: *Salvia nemerosa.*
Variety denomination: 'Florsalbro'.

BACKGROUND OF THE INVENTION

The new *Salvia* cultivar is a product of a planned breeding program conducted by the inventor, Tobias Bräunig, in Quedlinburg, Germany. The objective of the breeding program was to produce new *Salvia* varieties with denser plant habits, strong garden performance, in a range of flower colors. The open pollination resulting in this new variety was made during Summer of 2010.

The seed parent is an unpatented, proprietary, *Salvia nemerosa*. The pollen parent is unknown as it was an open pollination breeding program. The new variety was identified as a potentially interesting selection in Summer 2011, at a greenhouse in Quedlinburg, Germany.

Asexual reproduction of the new cultivar 'Florsalbro' by vegetative cuttings was first performed during 2011, at a research greenhouse in Quedlinburg, Germany. Subsequent propagation has shown that the unique features of this cultivar are stable and reproduced true to type on successive generations.

SUMMARY OF THE INVENTION

The cultivar 'Florsalbro' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Florsalbro' These characteristics in combination distinguish 'Florsalbro' as a new and distinct *Salvia* cultivar:

1. Dark rose flower color.
2. Compact plant form.
3. Abundant flowering.
4. Early flowering.

PARENT COMPARISON

Plants of the new cultivar 'Florsalbro' are similar to plants of the seed parent, in most horticultural characteristics, however, plants of the new cultivar 'Florsalbro' differ in the following:

1. Dark rose flower color. The seed parent has a light rose colored flower.
2. More vigorous growth rate.
3. More abundant flowering.
4. Earlier flowering.

COMMERCIAL COMPARISON

Plants of the new cultivar 'Florsalbro' can also be compared to the commercial variety *Salvia* 'Mainacht", unpatented. These varieties are similar in most horticultural characteristics; however 'Florsalbro' differs in the following:

1. More compact plant.
2. More inflorescences per plant.
3. Deeper bright rose color.

BRIEF DESCRIPTION OF THE PHOTOGRAPHS

Figure 1:
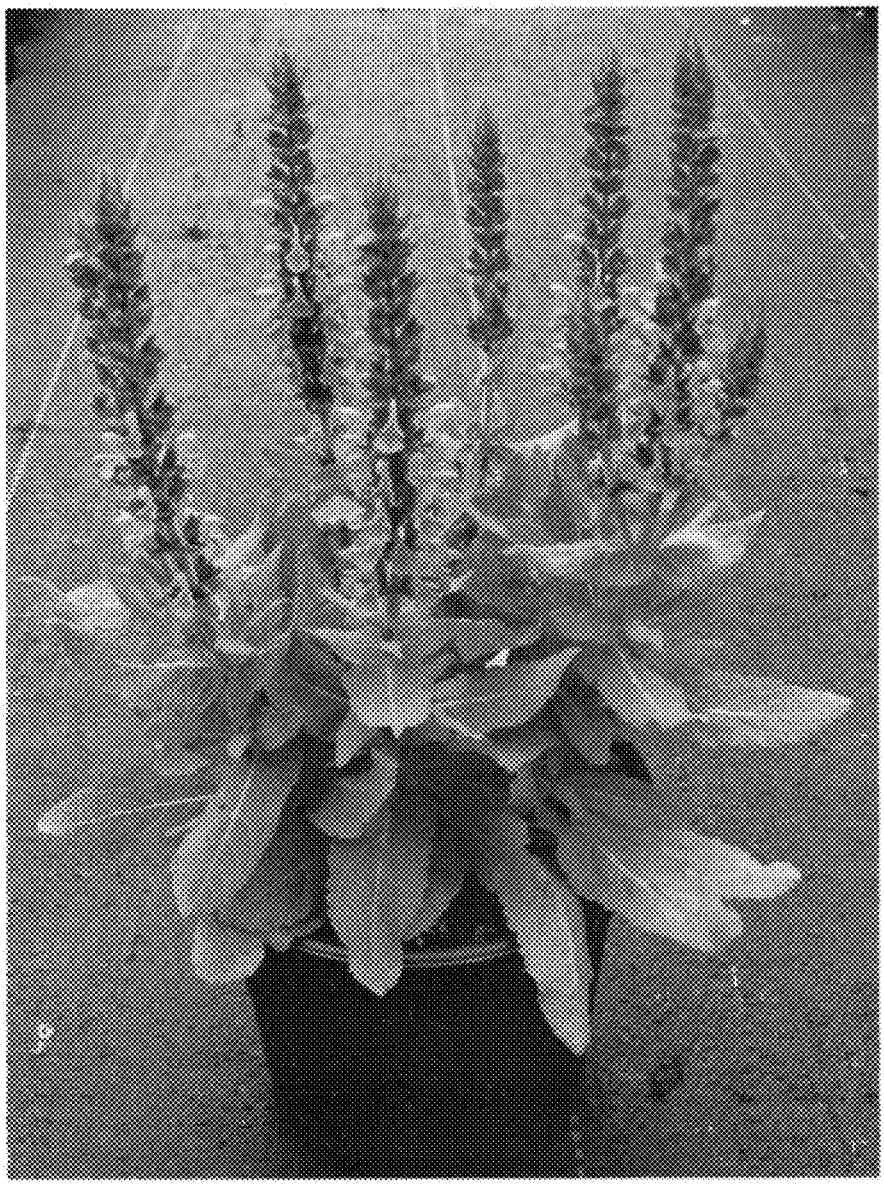

The accompanying photograph in FIG. 1 illustrates in full color a typical plant of 'Florsalbro', shown in an 8 inch commercial container.

Figure 2:
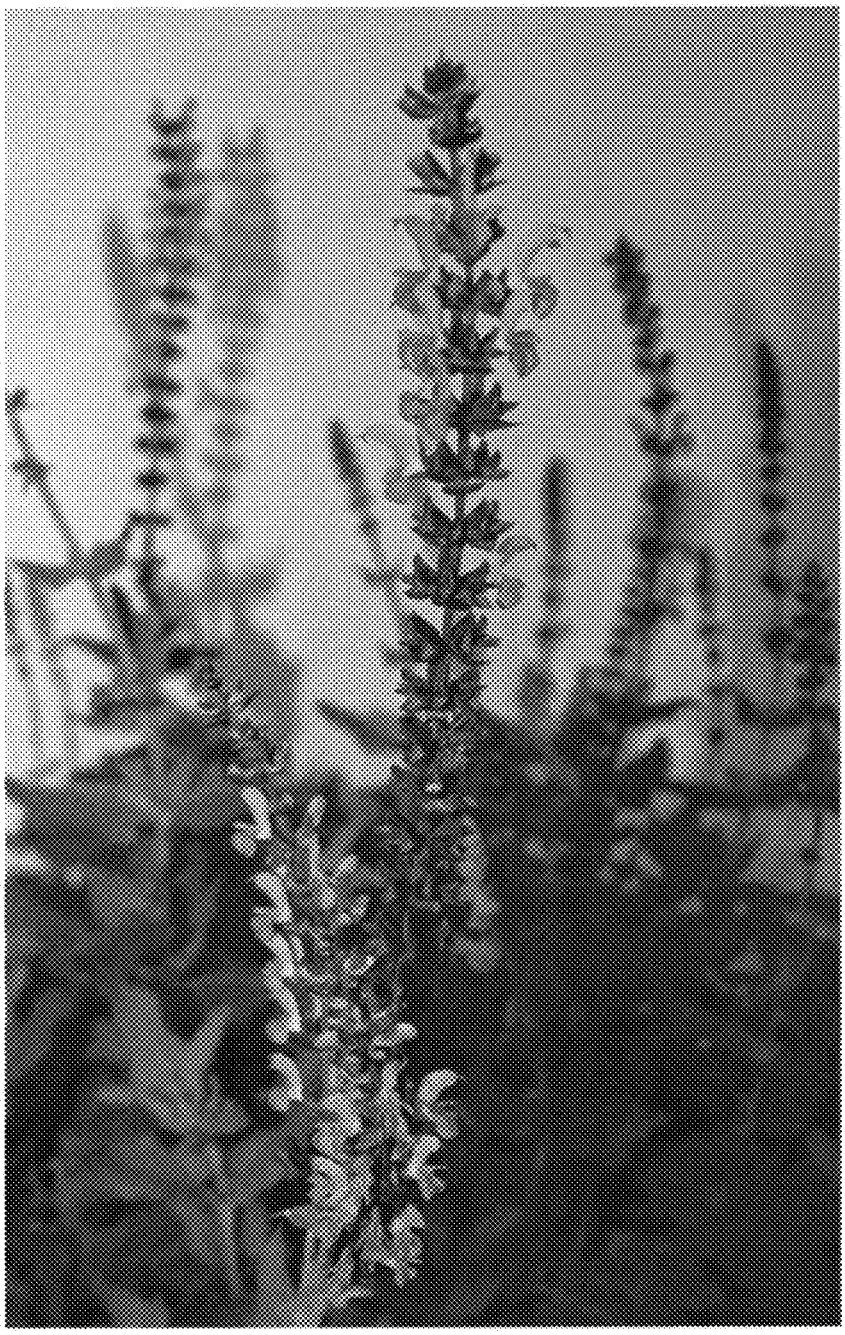

FIG. 2 illustrates in full color typical flowers 'Florsalbro'.

Plants were grown in a greenhouse. Santa Paula. Calif., in a commercial 8 inch container.

Age of the plant photographed is approximately 16 weeks from an unrooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Florsalbro' plants grown in a greenhouse in Santa Paula, Calif. The growing temperature ranged from approximately 10° C. to 30° C. The greenhouse is un-shaded, giving bright, normal sunlight conditions. Measurements and numerical values represent averages of typical plant types.

Botanical classification: *Salvia nemerosa* 'Florsalbro'.

PROPAGATION

Root description: Fine, densely fibrous. Colors include Green-White 157D on new growth and Orange-White 159C, Grey-Brown 199B and 199C for older roots.

PLANT

Growth habit: Upright perennial.

Pot size of plant described: 1 gallon pot.

Height: Approximately 32 cm to top of foliage. Approximately 48 cm to top of flowering plane. Measured from soil level of pot.

Plant spread: Approximately 50 cm.

Growth rate: Rapid.

Branching characteristics: Moderately well branched. Approximately 6 to 8 primary branches per plant.

Length of primary lateral branches: Approximately 28 cm.

Diameter of lateral branches: Approximately 0.35 cm.

Quantity of lateral branches: About 18 to 24.

Stem:

*Color*.—Near RHS Green 138A.

*Texture*.—Minute pubescence and ribbed.

Internode length: Average 5.5 cm.

Age of plant described: Approximately 20 weeks from 3 rooted cuttings.

FOLIAGE

Leaf:

*Arrangement*.—Opposite.

*Quantity*.—Approximately 12 fully expanded per main branch.

*Average length*.—Approximately 8.2 cm., including petiole.

*Average width*.—Approximately 3.3 cm.

*Shape of blade*.—Deltoid.

*Apex*.—Acute.

*Base*.—Truncate.

*Attachment*.—Stalked.

*Margin*.—Crenate.

*Texture of top surface*.—Matte, glabrous.

*Texture of bottom surface*.—Matte, glabrous, reticulate.

*Color*.—Young foliage upper side: Near RHS Green 137A. Young foliage under side: Near RHS Green 137D. Mature foliage upper side: Near RHS Green 137A. Mature foliage under side: Near RHS Green 138B.

*Venation*.—Type: Reticulate. Venation color upper side: Near RHS Yellow-Green 145B. Venation color under side: Near RHS Green 139D.

*Petiole*.—Average Length: Approximately 0.9 cm. Diameter: Approximately 0.1 cm. Color: Near RHS Green 139D.

FLOWER

Natural flowering season: Flowering from early Spring through late Summer.

Inflorescence type and habit: Flowers arranged in verticillasters on spikes.

Flower longevity on plant: Individual flowers last approximately 2 to 3 days on the plant. Each spike lasts approximately 4 weeks with flowers.

Quantity of flowers: About 12 buds and 20 fully opened flowers per spike, at one time. Mature plants have approximately 20 to 30 spikes.

Spike size:

*Diameter*.—Approximately 1.5 cm.

*Height*.—Approximately 12.0 cm.

Individual flowers:

Size:

*Diameter*.—Approximately 0.9 cm.

*Length*.—Approximately 1.7 cm.

*Persistence*.—Non-persistent.

*Fragrance*.—Faint.

Corolla:

*Petal arrangement*.—The corolla is sympetalous and typically bilabiate with 2 small, fully fused lobes forming a single, curved upper lip and 3 larger fused lobes forming a lower lip.

*Margin*.—Entire.

*Tip shape*.—Upper lip tip obtuse, lower lip tip retuse.

*Length*.—Upper lip Approximately 0.8 cm. lower lip Approximately 0.5 cm. Tube length Approximately 0.5 cm.

*Width*.—Upper lip Approximately 0.25 cm, lower lip Approximately 0.5 cm. Tube width Approximately 0.2 cm.

*Texture*.—Upper lip: Glabrous all surfaces.

*Lower lip*.—Glabrous all surfaces.

Color:

*Upper lip*.—When opening: Inner surface: Near RHS Red-Purple 68B. Outer surface: Near RHS Red-Purple 68B. Fully opened: Inner surface: Near RHS Red-Purple 73C. Outer surface: Near RHS Red-Purple 73A. Fading: Inner surface: Near RHS Red-Purple N74D. Outer surface: Near RHS Red-Purple N74C.

Color:

*Lower lip*.—When opening: Inner surface: Near RHS Red-Purple N74B. Outer surface: Near RHS Purple N78B. Fully opened: Inner surface: Near RHS Red-Purple 73B, Margin Red-Purple 64B. Outer surface: Near RHS Red-Purple 73B, Margin Red-Purple N74B. Fading: Inner surface: Near RHS Red-Purple 72B. Outer surface: Near RHS Red-Purple 72C.

Color:

*Tube*.—When opening: Inner surface: Near RHS White 155C. Outer surface: Near RHS White 155C. Fully opened: Inner surface: Near RHS White 155C. Outer surface: Near RHS White 155C. Fading: Inner surface: Near RHS White 155C. Outer surface: Near RHS White 155C.

Bud:

*Shape*.—Ovoid.

*Length*.—Approximately 0.6 cm.

*Diameter*.—Approximately 0.3 cm.

*Color*.—Near RHS Red-Purple 72C.

Calyx:

*Length*.—Approximately 0.6 cm.

*Diameter*.—Approximately 0.5 cm.

*Shape*.—Tubular.

Sepals:

*Shape*.—Quantity per flower: 3, fused to form a tube.

*Unfused apex*.—Length: Approximately 0.5 cm. Width: Approximately 0.6 cm.

*Margin*.—Entire.

*Apex*.—Acute.
*Texture*.—Softly pubescent.
*Color*.—Immature: Near RHS Green 138A, heavily flushed Purple N79A. Mature: Near RHS Green 137C, heavily flushed Purple N79A.

Peduncle:
*Length*.—Average 1.8 cm.
*Diameter*.—0.4 cm.
*Color*.—Near RHS Green 137C, blotched with. Purple N79A.
*Orientation*.—Upright, straight.
*Strength*.—Strong.
*Texture*.—Softly pubescent, ridged.

Pedicels:
*Length*.—Average 0.1 cm.
*Diameter*.—0.1 cm.
*Color*.—Near RHS Green 138A, heavily flushed Purple N79A.
*Orientation*.—Straight, approximately 45 degree angle from attachment.
*Strength*.—Flexible.
*Texture*.—Pubescent.

REPRODUCTIVE ORGANS

Stamens:
*Number*.—2.
*Filament length*.—Approximately 0.6 cm.
*Filament color*.—Near RHS Red-Purple 73D.

Anthers:
*Shape*.—Very narrowly elliptic.
*Length*.—Approximately 1 mm.
*Color*.—Near RHS Purple N79C.
*Pollen*.—Pollen production not observed.

Pistil:
*Number*.—1.
*Length*.—Approximately 0.8 cm.
*Style*.—Length: Approximately 0.5 cm. Color: Near RHS Red-Purple 73D.
*Stigma*.—Shape: Forked. Color: Near RHS Red-Purple 71A. Ovary color: Near RHS Green 137B.

OTHER CHARACTERISTICS

Seeds and fruits: Not observed to date.
Disease/pest resistance: Neither resistance nor susceptibility to pathogens and pests common to *Salvia nemerosa* have been observed.
Temperature tolerance: The new variety tolerates temperatures within USDA zones 3 to 8.

What is claimed is:

1. A new and distinct cultivar of *Salvia* plant named 'Florsalbro' as herein illustrated and described.

* * * * *